(12) United States Patent
Laurent-Applegate

(10) Patent No.: US 9,434,923 B2
(45) Date of Patent: Sep. 6, 2016

(54) PREPARATION OF PARENTAL CELL BANK FROM FOETAL TISSUE

(71) Applicant: CENTRE HOSPITALIER UNIVERSITAIRE VAUDOIS (CHUV), Lausanne (CH)

(72) Inventor: Lee Ann Laurent-Applegate, Bercher (CH)

(73) Assignee: CENTRE HOSPITALIER UNIVERSITAIRE VAUDOIS (CHUV), Lausanne (CH)

(*) Notice: Subject to any disclaimer, the term of this patent is extended or adjusted under 35 U.S.C. 154(b) by 0 days.

(21) Appl. No.: 14/620,321

(22) Filed: Feb. 12, 2015

(65) Prior Publication Data

US 2015/0152388 A1    Jun. 4, 2015

Related U.S. Application Data

(62) Division of application No. 14/131,736, filed as application No. PCT/IB2012/053512 on Jul. 10, 2012, now Pat. No. 8,986,678.

(30) Foreign Application Priority Data

Jul. 11, 2011 (EP) ..................................... 11173452

(51) Int. Cl.
| | | |
|---|---|---|
| A01N 63/00 | (2006.01) | |
| A01N 65/00 | (2009.01) | |
| C12N 5/00 | (2006.01) | |
| C12N 5/02 | (2006.01) | |
| C12N 5/077 | (2010.01) | |
| C12N 5/073 | (2010.01) | |
| A61K 35/32 | (2015.01) | |
| A61K 35/33 | (2015.01) | |
| G01N 33/50 | (2006.01) | |

(52) U.S. Cl.
CPC ............. *C12N 5/0655* (2013.01); *A61K 35/32* (2013.01); *A61K 35/33* (2013.01); *C12N 5/0603* (2013.01); *C12N 5/066* (2013.01); *G01N 33/5008* (2013.01); *G01N 2500/10* (2013.01)

(58) Field of Classification Search
None
See application file for complete search history.

(56) References Cited

U.S. PATENT DOCUMENTS

| | | |
|---|---|---|
| 2010/0233233 A1 | 9/2010 | Zheng |
| 2011/0008415 A1 | 1/2011 | Clement et al. |
| 2014/0193377 A1 | 7/2014 | Laurent-Applegate |

OTHER PUBLICATIONS

Gao et al., BioMed Res. Internat., pp. 1-8 (2014).*
Loeser, Matrix Bio., 39:11-16 (2014).*
Docheva et al., Mol. Cell Biol., 25(2):699-705 (2005).*
Stoll et al., J. Ortho. Res., Sep., 1170-1177 (2010).*
Jin et al., Ann. Dermatol., 24(1):16-21 (2012).*
Medical Dictionary <http://medical-dictionary.thefreedictionary.com/Interstitial+space> (Accessed Feb. 25, 2016).*
Zhang et al., Crit. Rev. Biomed. Eng., 37(1-2): 1-57 (2009).*
Frantz et al., J. Cell Sci., 123(24):4195-4200 (2010).*
Chang et al., Biomater., 24:4853-4858 (2003).*
Chang et al., Biomater., 27:1876-1888 (2006).*
Fan et al., Biomater., 27:4573-4580 (2006).*
Hollister, Nature Mater., 4:518-590 (2005).*
Iwasa et al., Knee Surg. Sports Traumatol. Arthrosc., 17:561-577 (2009).*
Temenoff et al., Biomater., 21:431-440 (2000).*
Zhao et al., J. Zhejiang Univ., Biomedic., Biotech. B, 16(11):914-923 (2015).*
Bea, H., et al. (2008), "Human fetal chondrocyte transplants for damaged intervertebral disc", *The Spine Journal*, 8: 92S-93S.
Brink, H.E., et al. (2004), "Serum-Dependent Effects on Fetal and Adult Tendon Fibroblast Migration and Collagen Production", *50th Annual Meeting of the Orthopaedic Research Society*, Poster No. 0871.
Brink, H.E., et al. (2005), "Influence of Serum on Adult and Fetal Dermal Febroblast Migration, Adhesion, and Collagen Expression", *In Vitro Cell. Dev. Biol.—Animal*, 41:252-257.
Cetinkaya, G., et al. (2011), "Derivation, characterization and expansion of fetal chrondrocytes on different microcarriers", *Cytotechnology*, 63:633-643.
Cucchiarini, M., et al. (2005), "Gene therapy for cartilage defects", *The Journal of Gene Medicine*, 7:1495-1509.
Darwiche, S.E., et al., (2010), "Fetal Epiphyseal Chondrocyte Master Cell Banking for Osteochondral Repair and Regineration", *European Cells and Materials*, 20(2): 39.
International Preliminary Report on Patentability dated Jan. 14, 2014 issued in PCT Patent Application No. PCT/IB2012/053512.
International Search Report dated Oct. 15, 2012 issued in PCT Application No. PCT/IB2012/053512.
Izumi, T., et al. (2000),"Chondrocyte transplantation for osteochondral defects with the use of suspension culture" *Cell and Tissue Banking*, 1: 207-212.
Maffulli, N., et al. (2000), "Tenocytes from ruptured and tendinopathic achilles tendons produce greater quantities of type III collagen than tenocytes from normal achilles tendons", *The American Journal of Sports Medicine*, 28(4):499-505.
Moulin, V., et al. (2001), "Fetal and Adult Human Skin Fibroblasts Display Intrinsic Differences in Contractile Capacity", *Journal of Cellular Physiology*, 188:211-222.

(Continued)

*Primary Examiner* — Thomas J Visone
(74) *Attorney, Agent, or Firm* — Harness, Dickey and Pierce, P.L.C.

(57) ABSTRACT

The present invention relates to methods of in vitro preparation of a parental cell bank (PCB) from foetal tissue consisting of foetal epiphyseal tissue, foetal Achilles tendon tissue and foetal skin tissue, using a rapid mechanical primary cell culture selection of cell type to be used in methods for wound and tissue repair.

18 Claims, 11 Drawing Sheets

(56) References Cited

OTHER PUBLICATIONS

Office Action dated Apr. 23, 2014 issued in U.S. Appl. No. 14/131,736.

Office Action dated Jul. 3, 2014 issued in U.S. Appl. No. 14/131,736.

Peterson, W., et al. (2002), "Angiogenesis in fetal tendon development: spatial and temporal expression of the angiogenic peptide vascular endothelial cell growth factor", *Anat. Embryol.* 205: 263-270.

Pufe, T., et al., (2001), "The angiogenic peptide vascular endothelial growth factor is expressed in foetal and ruptured tendons", *Virchows Archives*, 439: 579-585.

Pufe, T., et al., (2003), "The angiogenic peptide vascular endothelial growth factor (VEGF) is expressed in chronic sacral pressure ulcers", *Journal of Pathology*, 200: 130-136.

Rajabalian, S., et al. (2003), "Supportive effects of human embryonic fibroblast cell lines on growth and proliferation of EBV-transformed lymphoblastoid cells", *Iranian Biomedical Journal*, 7(4):147-153.

Reginato, A., et al. (1994), "Formation of nodular structures resembling mature articular cartilage in long-term primary cultures of human fetal epipheseal chondrocytes on a hydrogel substrate", *Arthritis and Rheumatism*, 37(9): 1338-1349.

Roche, S., et al. (2001), "Native and DPPA cross-linked collagen sponges seeded with fetal bovine epiphyseal chondrocytes used for cartilage tissue engineering", *Biomaterials*, 22: 9-18.

Thyberg, J., et al. (1977), "Fine structure of rabbit ear chondrocytes in vitro and after autotransplantation", *Cell Tiss. Res.*, 180: 341-356.

Tohidnezhad, M., et al. (2011), "Platelet-released growth factors can accelerate tenocyte proliferation and activate the anti-oxidant response element", *Histochemistry and Cell Biology*, 135: 453-460.

Tracy, E.C., et al. (2011), "Cell-type selective phototoxicity achieved with chlorophyll-a derived photosensitizers in a co-culture system of primary human tumor and normal lung cells", *Photochem Photobiol*, 87(6):1405-1418.

\* cited by examiner

Enzymatic digestion

Chondro-Progenitor Cell Growth

Recovery WCB

Chondro-Progenitor Characterization

PREPARATION OF PARENTAL CELL BANK FROM FOETAL TISSUE

PRIORITY STATEMENT

This application is a divisional of pending U.S. application Ser. No. 14/131,736 filed on 9 Jan. 2014, which claims priority to PCT International Application No. PCT/IB2012/053512 which has an International filing date of 10 Jul. 2012 and claims priority under 35 U.S.C. §119 to European Application No. 11173452.1 filed 11 Jul. 2011. The contents of each application recited above are incorporated herein by reference in their entirety.

FIELD OF THE INVENTION

The present invention relates to methods of in vitro preparation of a parental cell bank (PCB) from foetal tissue consisting of foetal epiphyseal tissue, foetal Achilles tendon tissue and foetal skin tissue, using a rapid mechanical primary cell culture selection of cell type to be used in methods for wound and tissue repair.

BACKGROUND OF THE INVENTION

Cellular therapy is becoming an interesting addition for medical therapies for repairing, restoring or ameliorating function of tissues and particularly combining with traditional surgical techniques. Some cell choices are more adaptable to cellular therapy in patients. Tissue choices from animal and human at all ages of development can be evaluated with advantages and disadvantages for each final cell type. Current restrictions for human cell-based therapies have been related to technological limitations with regards to cellular proliferation capacity (simple culture conditions), maintenance of differentiated phenotype for primary human cell culture, transmission of communicable diseases and the consistency and stability of the selected population of cells depending on their isolation procedure. Cultured primary foetal cells from one organ donation meet the exigent and stringent technical aspects for development of therapeutic products. Master and working cell banks from one foetal organ donation can be developed in short periods of time and safety tests can be performed at all stages of cell banking.

Cell therapy has been proposed as a less invasive alternative or combined therapy for surgical procedures and tissue engineering of specific tissues. Several cell types have been investigated to be utilized in cell therapy: embryonic stem cells (ES), umbilical cord cells, foetal cells and adult stem cells (from bone marrow-haematopoitic stem cells or HSCs and marrow stem cells or MSCs) along with adipose tissue, platelets, placenta and amniotic fluid cells. As for any application in tissue engineering, the cell origin and type are essential aspects. Each type of cell requires different methods to manipulate their differentiation and self-renewal capabilities for specific therapies with various advantages and disadvantages.

Foetal cells have been used extensively in biology and medicine for many years without much public knowledge for their importance, especially in the development of necessary vaccines. Foetal cells are differentiated cells with high expansion, regeneration and low immunogenic properties. They can be isolated from foetal tissues, which follow embryonic stage after 9 weeks of development. Foetal skin cells offer an ideal solution for effective and safe cell therapy and tissue engineering for several reasons including; a) cell expansion capacity from one organ donation; b) minimal cell growth requirements; c) adaptation to biomaterials for delivery; and, d) resistance to oxidative stress. Foetal skin cells have extensive expansion possibilities as it requires only one organ donation (1-4 $cm^2$ tissue) to create enough frozen cells to produce a bank capable of hundreds of thousands of treatments (i.e. for skin, over 35 billion fetal skin constructs 9×12 cm, can be produced from one dedicated cell bank). Also, cell culture requirements are minimal compared to stem or mesenchymal cell types. As the foetal skin cells are already differentiated and do not need to be directed or altered, the vast number of additional growth factors normally necessary are not needed for cell culture and expansion. For cell banking, careful selection of a donor and an extensive screening of both the donor and cultured cells to avoid transmissible viral, fungal or bacterial disease provide a safe and secure utilization of foetal cells for therapeutic usage. In addition, foetal cells, unlike neonatal, young or adult cells adapt particularly well to biomaterials allowing efficient and simple delivery to the patient. It has been shown that cells from donors (neonatal to adult) are not capable of efficient integration into various biomaterials and some biomaterials are, in fact, toxic to the cell. It is true that the scaffold is very important for tissue engineering, but the cell type is most probably the limiting factor. For processing of a final product for clinical delivery, both the homologous distribution and the rapidity of development of the final product are major significant advantages. When long culture periods are necessary as for autologous grafting or for the commercially available products to date, there is a non-negligible increased risk for contamination. It is also important to have a process that is consistent and easily repeated. By developing consistent cell banks with fetal cells, many of the risk factors can be eliminated for bringing safe and effective human cell-based therapies to the bedside.

Key elements including identity, purity, sterility, stability, safety and efficacy are recommended for cellular-based products. In all, the new regulations impose strict criteria for the production and the environment used for the production of cell-based products to be used in clinical trials and treatments. Current restrictions for human cell-based therapies have been related to technological limitations with regards to cellular proliferation capacity (simple culture conditions), maintenance of differentiated phenotype for primary human cell culture, transmission of communicable diseases and the consistency and stability of the selected population of cells depending on their isolation procedure. Cultured primary foetal cells from one organ donation meet the exigent and stringent technical aspects for development of therapeutic products. Master and working cell banks from one foetal organ donation can be developed in short periods of time and safety tests can be performed at all stages of cell banking. For therapeutic use, foetal cells can be used up to two thirds of their life-span in an out-scaling process and consistency for several biological properties includes protein concentration, gene expression and biological activity are ensured.

The relatively simple manipulation of foetal cells, related to their collection, culture expansion and storage has made foetal cells an attractive choice for cell therapy. Unlike ES cells, foetal cells do not form tumours and seem to lack immunogenecity when transplanted. In contrast with mesenchymal stem cells to date, foetal cells do not require feeder layers for growth or specific growth factors for differentiation. One organ donation is capable of producing a consistent, Master Cell Bank (MCB) that would be available for hundreds of thousands of patient treatments. The fully-defined consistent cell bank could easily be assessed for safety concerning any potential virus and pathogens in parallel to the original organ donation where serology and pathology are accomplished.

Primary cultures of foetal differentiated cells from specific tissues such as cartilage, tendon and skin which specific cell sources can be developed including chondrocytes (chondro-progenitors), skin fibroblast progenitors, and tendon progenitors determine the quality of the clinical cell bank developed. It is well accepted that the initial treatment of the tissue is of major importance to the physiological properties of the cells thereafter produced. The routine state-of-the-art in primary culture is to enzymatically digest the small pieces of tissue to liberate all live cells for cell culture. This is particularly used for "hard" tissues, but also for soft tissues, where multiple digestion steps are used routinely. By doing this, a completely different population of cells is liberated and cultured in the primary and secondary cell cultures (Carrascosa A, Audi L, Ballabriga A Pediatric Research 19:720-727, 1985; Roche S et al, Biomaterials 22:9-18, 2001; Bae H. et al., The Spine Journal Vol. 8, No. 5, pages 92S-93S, 2008; Reginato A. M. et al., Arthritis and Rheumatism, Vol. 37, No. 9, 1994).

However, it is also known that the enzymatic treatment causes inconsistencies, develops populations of cells with different morphologies, physiological properties, stability, and function (Diaz-Romero J, Gaillard J-P, Grogan P, Nesic, Trub T, Varlet P-M J Cellular Physiol 202:731-742, 2005).

The avascular, aneural and alymphatic nature of articular cartilage has made repair of this tissue a challenge for both surgeons and tissue engineers. A gold standard for osteochondral therapeutic strategies, especially for the choice of cell source remaining a central and controversial issue, is far from being determined. Adult mesenchymal stromal cells (MSCs) are, to date, the most used cell source, despite concerns of phenotypic homogeneity, reliability and stability.

Treatment of osteoarthritic defects needs to be improved as no satisfactory therapeutic solution exists to date. It is especially crucial to develop new solutions to avoid premature degeneration of the cartilage to avoid total joint replacement. Development of new cellular assisted surgical techniques is based on a defined cellular banked product that can meet the requirements for stringent therapeutic agent preparation.

Thus there is still a need to develop methods for producing new tissues such as tendon, cartilage, other musculoskeletal tissues, and skin, for use in the therapeutic strategies. More specifically there is a need to develop cell banks which provide more stable and uniform population of cells and to find an appropriate source of cells, that do not risk triggering an immune response, and that do not carry any infectious agents.

SUMMARY OF THE INVENTION

To solve the above-identified problem, Applicants have established a non-enzymatic method to liberate mechanically and rapidly early adherent cell populations that define the characteristics of a parental cell bank (PCB) establishment. In some embodiments, the primary, differentiated cells come from specific cartilage tissue, specific tendon tissue and specific skin tissue. To one skilled in the art, other embodiments could include primary differentiated cells from skin and musculoskeletal tissues such as, tendon, bone, muscle and vertebral disc. The development of the PCB allows consistent and stable further cell banking to be accomplished.

Specifically in one embodiment the present invention provides an in vitro non-enzymatic method for isolation, expansion and development of foetal cells selected from the group consisting of foetal epiphyseal chondrocytes, foetal Achilles tenocytes or foetal skin fibroblasts, comprising the steps of:
a) using foetal sample selected from ulnar foetal cartilage comprising foetal epiphyseal chondrocyte; foetal Achilles tendon comprising foetal Achilles tenocytes; or foetal abdominal skin comprising foetal skin fibroblasts;
b) micro-dissecting and dispersing said ulnar foetal cartilage, foetal Achilles tendon or foetal abdominal skin sample by mechanical attachment to scalpel scored surface;
c) culturing said ulnar foetal cartilage, foetal Achilles tendon or foetal abdominal skin sample in vitro under conditions wherein said foetal epiphyseal chondrocytes, foetal Achilles tenocytes or foetal abdominal skin fibroblasts proliferate,
d) selecting and isolating first adherent foetal epiphyseal chondrocyte cell populations, first adherent foetal Achilles tenocyte cell populations and first adherent foetal skin fibroblast populations therefrom.

In another embodiment, the present invention provides foetal cells obtained by the non-enzymatic method of the invention, such as foetal epiphyseal chondrocyte cell line having the designation FE002-Cart and deposited under accession number ECACC 12070303-FE002-Cart, foetal Achilles tenocyte cell line having the designation FE002-Ten and deposited under accession number ECACC 12070302-FE002-Ten and foetal skin fibroblast cell line having the designation FE002-SK2 and deposited under accession number ECACC 12070301-SK2. All deposits were made on 3 Jul. 2012 at the European Collection of Authenticated Cell Cultures (ECACC), located in the Public Health England Building, Porton Down, Salisbury SP4 0JG, United Kingdom.

In another embodiment, the present invention provides a use of foetal cells obtained by the method of the present invention for the production of new cartilage tissue and/or three dimensional constructs, new tendon tissue and/or three dimensional constructs, new skin tissue and/or three dimensional constructs, by using the differentiated cartilage, tendon or skin cells integrated into various matrixes.

In another embodiment, the present invention provides the foetal cells obtained by the method of the present invention for use as therapeutic agent.

In another embodiment, the present invention provides foetal cells obtained by the method of the present invention for use in a method for repair and regeneration of osteochondral tissue and musculoskeletal tissue, for use in a method for repair and regeneration of tendon tissue and musculoskeletal tissue, and for use in a method for repair and regeneration of skin tissue and for treating burns, wounds and fibrotic condition.

In another embodiment, the present invention provides foetal cells obtained by the method of the present invention for use in a method for treating osteochondral diseases or defects, arthritis and musculoskeletal diseases; for use in a method for treating musculoskeletal diseases and tendonopathies; for use in a method for treating skin diseases.

In further embodiment of the present invention is provided a screening method for development of therapeutic agents and/or medical devices for the treatment of arthritic, osteochondral defects, cartilage repair, tendon repair, musculoskeletal tissue repair and skin repair, comprising the use of foetal epiphyseal chondrocyte (FEC), foetal Achilles tenocytes or foetal skin fibroblasts obtained by the non-enzymatic method of the invention.

DETAILED DESCRIPTION OF THE INVENTION

Figure 1:
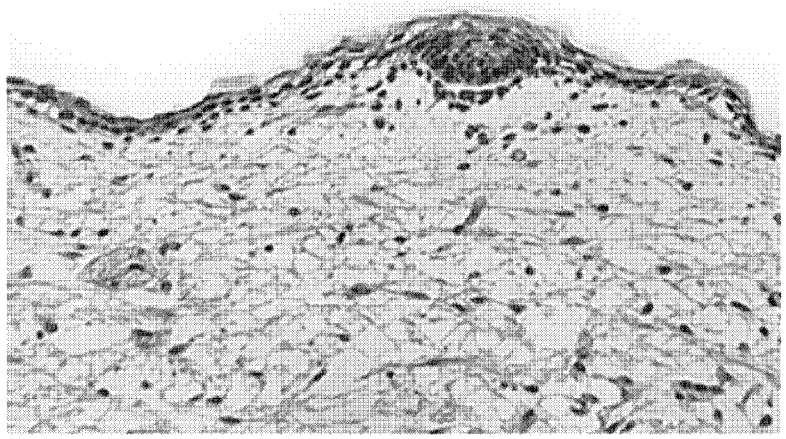
FIG. 1 shows tissue biopsy to begin Parental Cell Bank production for foetal skin progenitors and cell selection at Day 4 showing consistency.
Figure 1:
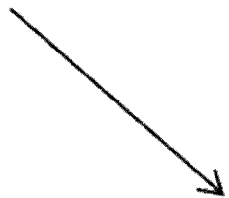
Figure 1:
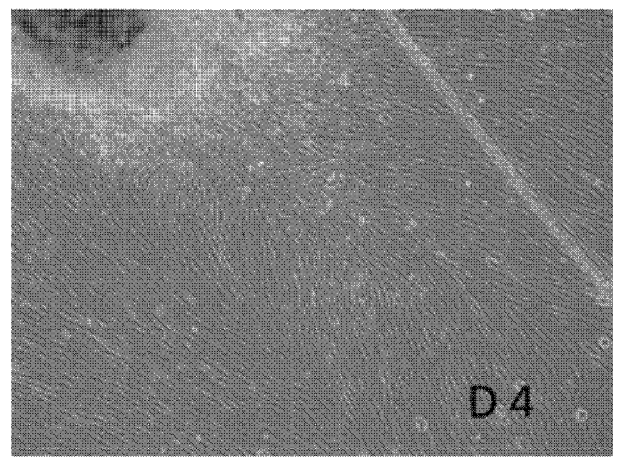
Figure 2:
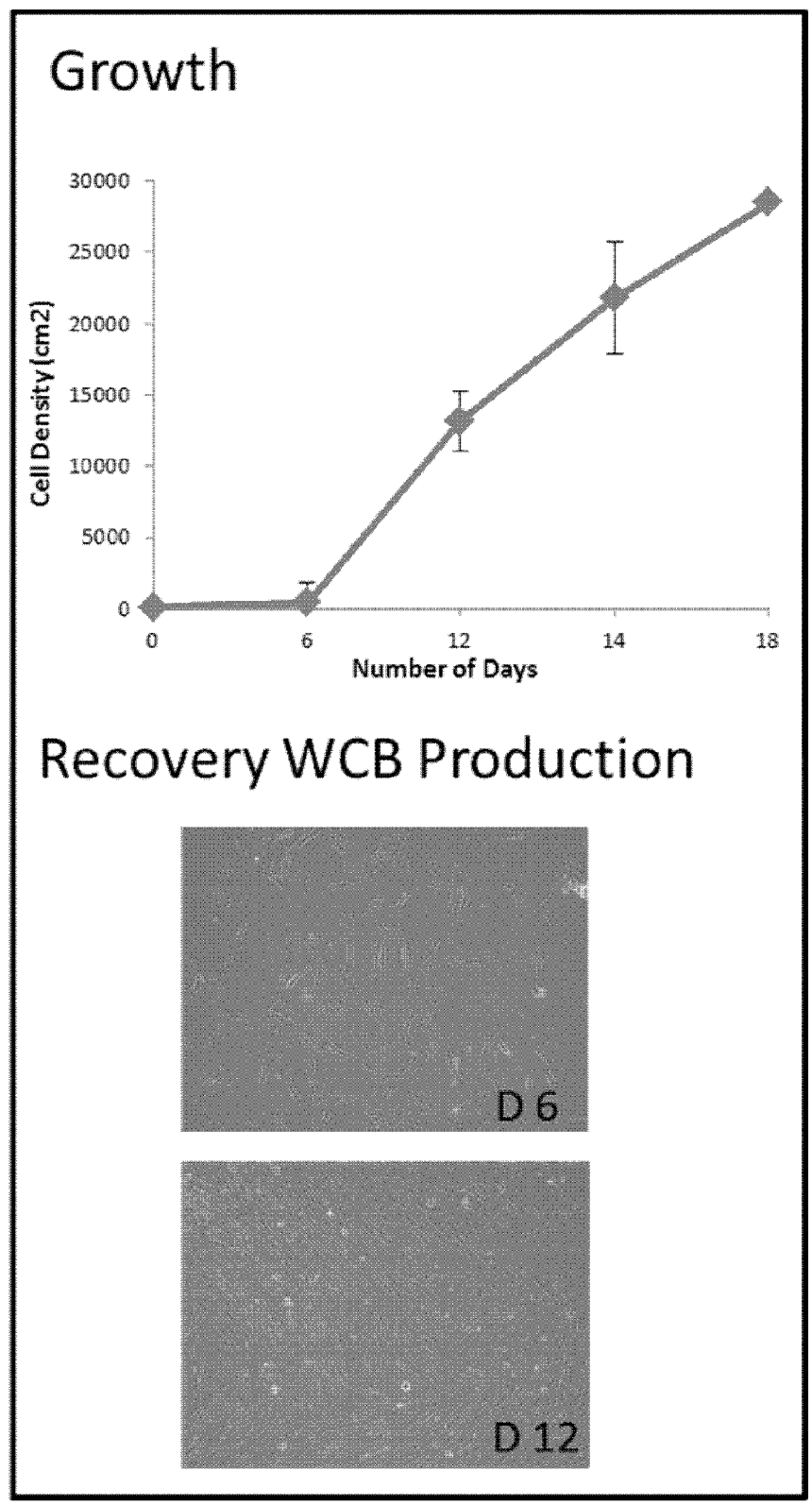
FIG. 2 shows cell growth of foetal skin progenitors following low density seeding (~2000 cells/cm$^2$) and recovery of frozen cell stocks at Day 6 and 12 showing high stability, consistency and maintained function.
Figure 3:
FIG. 3 shows morphological and growth differences of cell population selection if tissue is enzymatically digested to prepare Parental Cell Banks and non-consistency of cell population.
Figure 3:
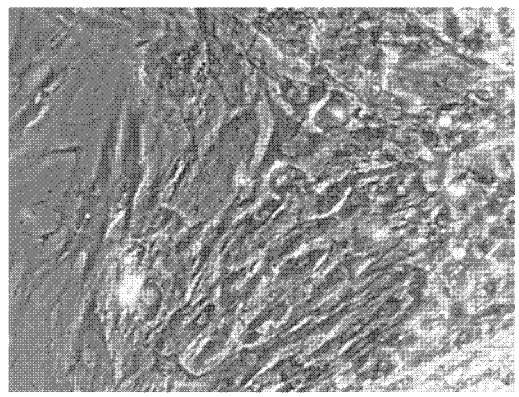
Figure 4:
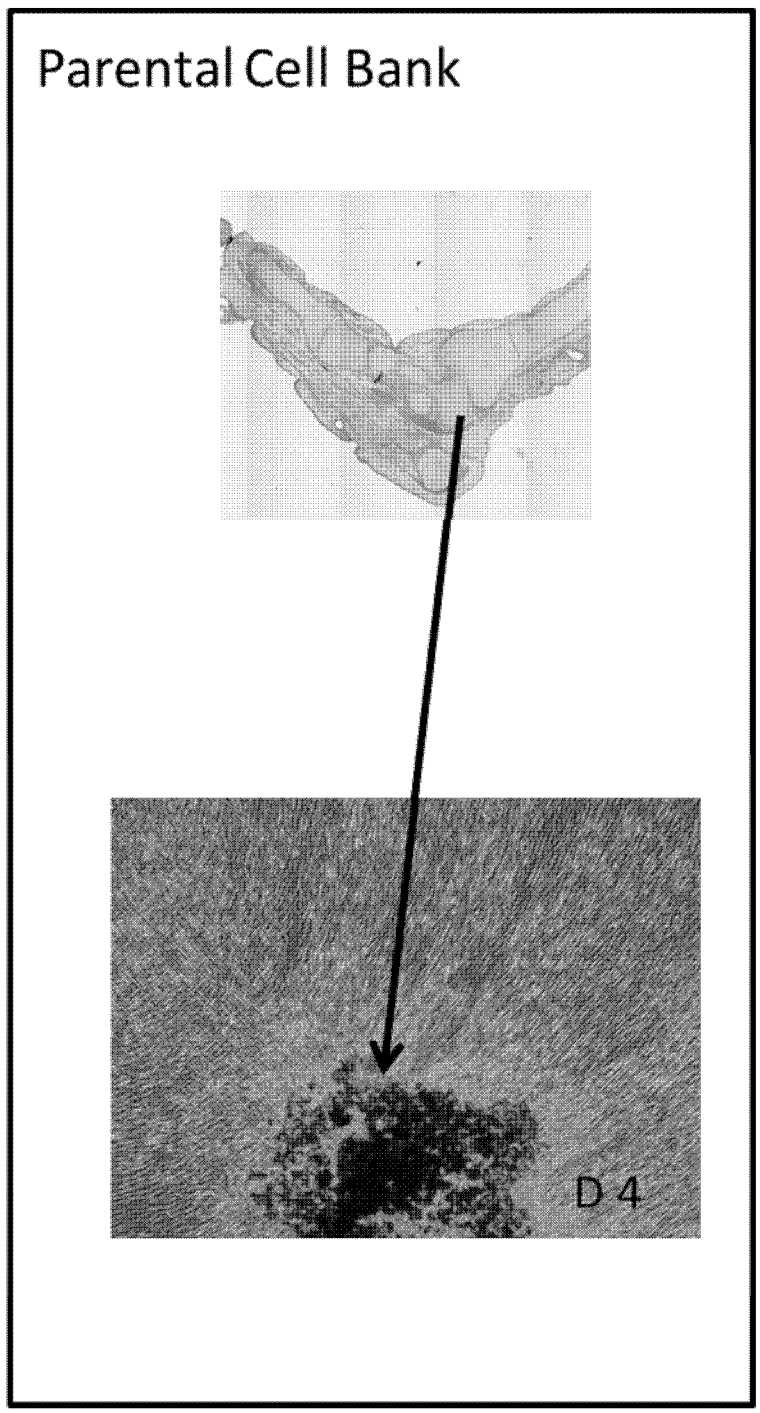
FIG. 4 shows tissue biopsy to begin Parental Cell Bank production for foetal tendon progenitors (foetal Achilles tenocytes) and cell selection at Day 4 showing consistency.
Figure 5:
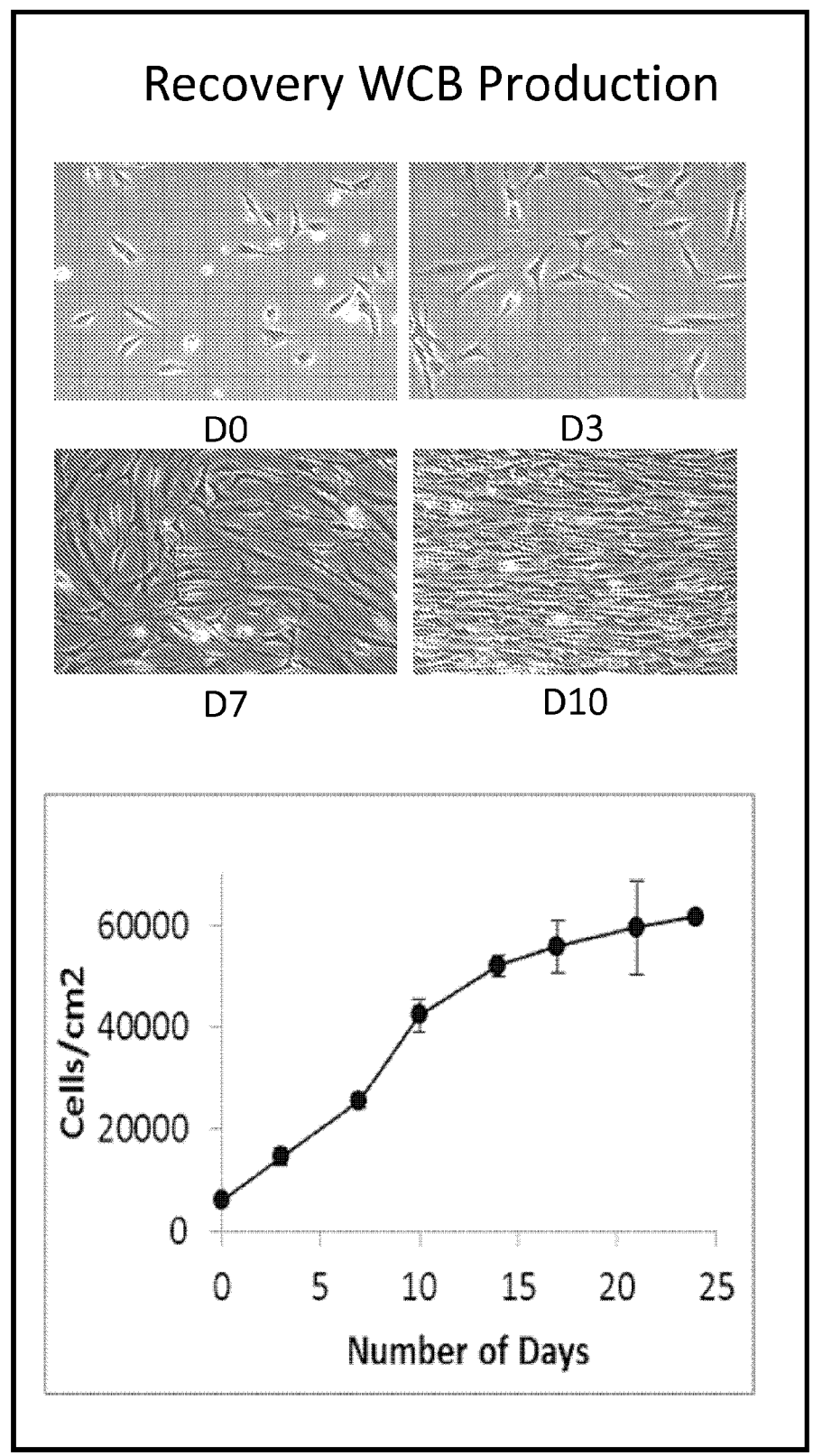
FIG. 5 shows cell growth of foetal tendon progenitors following low density seeding (~2000 cells/cm$^2$) and recovery of frozen cell stocks at Day 0, 3, 7 and 10 showing high stability, consistency and maintained function.
Figure 6:
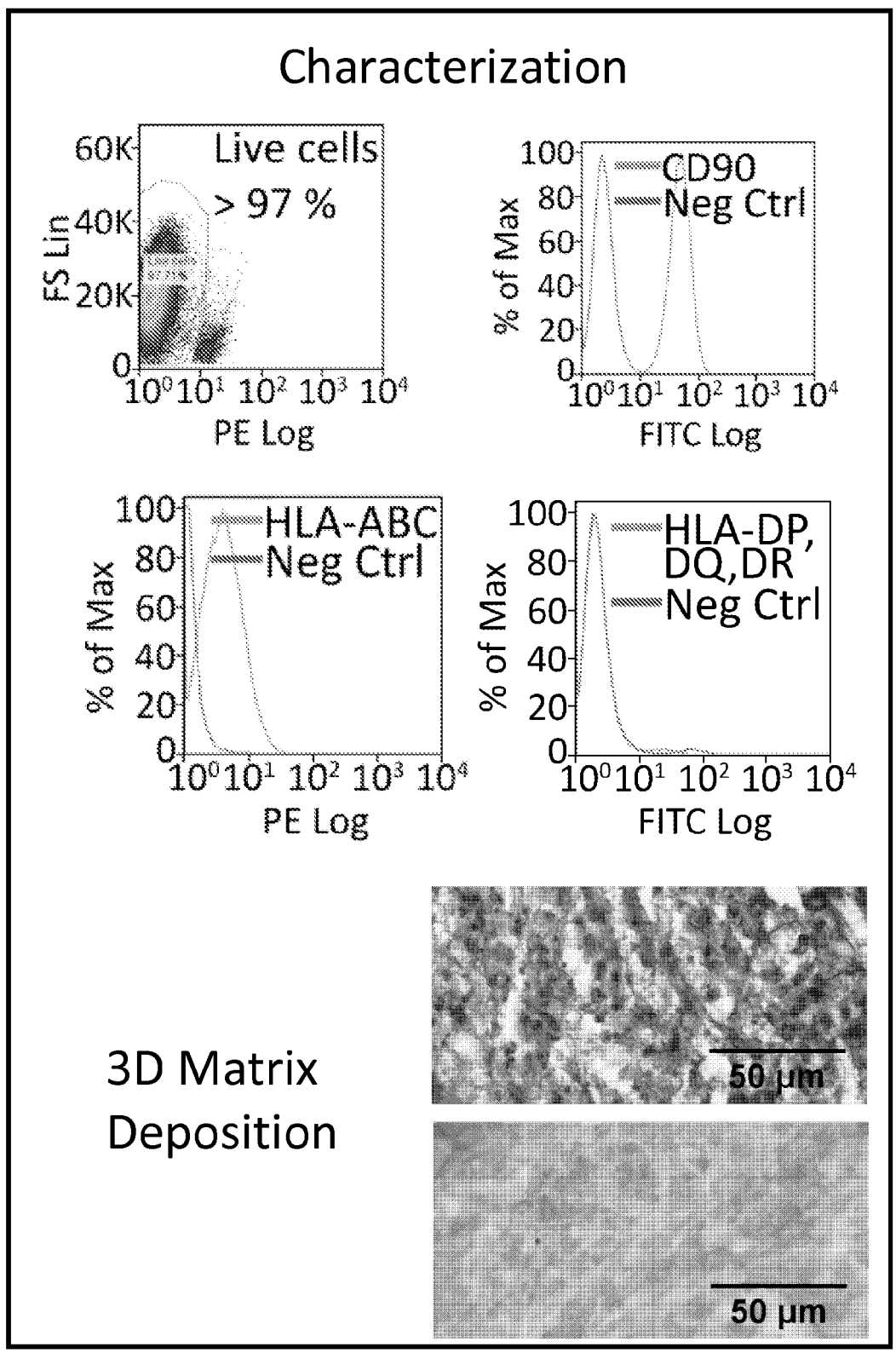
FIG. 6 shows FACS analysis and 3D matrix deposition characteristics for foetal tendon progenitors.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

As herein used, "a" or "an" means "at least one" or "one or more."

The term "comprise" is generally used in the sense of include, that is to say permitting the presence of one or more features or components.

The term "biomaterial" means a natural or synthetic material, including metals, ceramics and polymers devoid of deleterious effects when in contact with cells or biological tissues. Usually, the biomaterial support is selected from the group consisting of polymeric support comprising olefin polymers, fluorine polymers, polystyrene, polyacrylic polymers, polyesters polymers, polyurethane polymers, silicon polymers, cellulose polymers, epoxy polymers, silicone-based polymers, synthetic hydrogels, polycarbonates; biocompatible metallic supports comprising titanium and titanium alloys, nitinol, zirconia, stainless steel and cobalt chromium, alumina-zirconia composites; and/or biocompatible ceramics comprising porcelain, hydroxyapatite, and mixtures thereof.

The term "foetal chondrocyte or chondro-progenitor", "foetal Achilles tenocyte or foetal tendon progenitor" or "foetal fibroblast or foetal skin progenitor" means differentiated cells compared to undifferentiated foetal cells. Contrary to the present invention, the term "undifferentiated" is used to describe an immature or primitive cell. For example, undifferentiated foetal skin cells include those that can differentiate into dermal fibroblasts and epidermal keratinocytes or even other specific cell types of unrelated tissue. Differentiated cells are those that when placed in differentiation media specific for another cell type or into a different micro-environment, will not de-differentiate into a different cell lineage. For instance, if foetal skin fibroblasts are placed into osteogenic differentiation media, they will not become a whole population of osteoblasts or if they are placed in adipogenic media they will not become a whole population of adipocytes and if the same cells are placed into a 3D matrix in association with bone, will not de-differentiate into a whole population of osteoblasts because of the change in environment. These defined, differentiated cells have then major advantages for their potential use as therapeutic agents for both human and veterinary medicine.

The term "appropriate culture conditions" or "conditions in which foetal epiphyseal chondrocytes or chondro-progenitors, foetal tendon progenitors or foetal skin progenitors proliferate" is a medium for culturing cells containing nutrients that promote proliferation. The nutrient medium may contain any of the following in an appropriate combination and in the appropriate concentrations: isotonic saline, buffer, amino acids, serum or serum replacement, and other exogenously added factors. Those skilled in the art will recognize that any commonly employed culture conditions can be used. Methods for the selection of the most appropriate culture medium, medium preparation, and cell culture techniques are well known in the art and are described in a variety of sources, including Doyle et al., (eds.), 1995, Cell & Tissue Culture: Laboratory Procedures, John Wiley & Sons, Chichester; and Ho and Wang (eds.), 1991, Animal Cell Bioreactors, Butterworth-Heinemann, Boston, which are incorporated herein by reference. For example any appropriate type of culture medium can be used to isolate the foetal epiphyseal chondrocytes of the invention, such as, but not limited to, DMEM, McCoys 5A medium (Gibco), Eagle's basal medium, CMRL medium, Glasgow minimum essential medium, Ham's F-12 medium, Iscove's modified Dulbecco's medium, Liebovitz' L-15 medium, and RPMI 1640, serum-free media among others. The culture medium may be supplemented with one or more components including, for example, fetal bovine serum (FBS), defined growth factor serum replacements, equine serum (ES), HUMAN SERUM (HS), defined cell culture growth factors and one or more antibiotics and/or antimycotics to control microbial contamination, such as, for example, penicillin G, streptomycin sulfate, amphotericin B, gentamicin, and nystatin, either alone or in combination, among others.

The term "cell line" refers to a permanently established cell culture that will proliferate indefinitely given appropriate fresh medium and sufficient space. The term primary cell line refers to an established cell culture with limited passage numbers.

The term "cell bank" refers to harvesting biopsies from donor foetal tissue, such as ulnar foetal cartilage, foetal Achilles tendon or foetal skin; growing the foetal tissue and proliferating foetal cells to a high concentration under appropriate culture conditions; using enzymatic or non-enzymatic treatments (i.e. trypsin) to the tissue and cells of the resulting cultures to allow their suspension; pooling the suspended cells to make a generally uniform suspension of cells from the culture; gently mixing with a cryoprotectant; sealing aliquots of the cell suspension in ampoules; and freezing the aliquots. The optimal rate of freezing may be determined empirically. For example by decreasing the temperature of the ampoule by 1° C./min until −80° C. and then transferred to −160° C. approximately 24 hours later, or in programmed cycles in a automatic, calibrated Nano-Freezer for full cycle freezing to −165° C. This ultra-cold temperature bank preserves the cells such that they stop aging, thereby allowing them to retain the function and activity they had on the day they were collected.

The cryopreserved cells of the invention constitute a cell bank (1-10$^7$/ml), portions of which can be "withdrawn" by thawing and then used to produce new cartilage cells and tissue as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10% FBS. It is advisable that the cells in the culture medium be adjusted to an initial density of about 1-6×10$^{3-4}$ cells/ml. Once in culture, the cells may be examined daily, for example, with an inverted microscope to detect cell proliferation, and subcultured as soon as they reach an appropriate density or be monitored in real-time with scanning microscopy for quality control.

The cells of the invention may be withdrawn from the bank as needed, and used for the production of new cartilage, tendon or skin tissue or cells either in vitro, for example, as a three dimensional cartilage, tendon or skin culture, as described herein, or in vivo, for example, by direct administration of cells to the site in a subject where new cartilage, new tendon or new skin tissue or cells are needed.

The term "subject" (as in treatment of "a subject") or "patient" is intended to refer to a mammalian individual afflicted with, prone to, or suffering a condition, defect, disorder or disease (as specified herein). The term does not denote a particular age or sex. Thus, adult and newborn subjects, whether male or female, are intended to be covered. This term also includes both humans and animals. For example, the subjects can be, e.g., humans, non-human primates, wildlife, dogs, cats, horses, cows, pigs, sheep, goats, rabbits, rats, or mice. Preferably subjects are humans and horses. As used herein, the term wildlife includes any mammals, birds, amphibians or fish that are not domesticated. Examples of such wildlife include, but are not limited to, badgers, beavers, lions, tigers, bears, hawks and deer.

A three dimensional matrix means any matrix selected from a collagen matrix or PLA, PLGA, PEG, chitosan, elastin, hydrogel including for example HA (hyaluronic acid), silicone, chitosan or a mixture thereof. The matrix provides a three dimensional space to assure proper coverage and delivery of foetal cells, such as foetal epiphyseal chondrocytes or chondro-progenitors, foetal tendon progenitors, foetal skin progenitors, or foetal products to or also in association with an additional implant material. In one embodiment, the method of the invention allows preparation of three dimensional constructs using the differentiated cartilage, tendon or skin cells integrated into various matrixes. The integration of the differentiated cartilage, tendon or skin cells with matrix can occur by mixing, combining, pipetting, seeding, plating or placing the cells within a matrix.

The term "collagen" refers to a polypeptide compound, which is hydrophilic in nature that is subject to degradation by extracellular enzymes. Because, this substance is well studied, many key parameters can be controlled. Collagen is a weak antigen, thereby resulting in minimal rejection potential. A preferred collagen used in the methods and uses of the invention is horse collagen or porcine collagen.

An "implant" can be considered as a medical device that is to replace a missing biological structure, support a damaged biological structure, or enhance an existing biological structure. Implants can be made of artificial or natural materials. Medical implants are man-made devices and the surface of implants that contact the body might be made of a biomedical material such as titanium, silicone, polymers, apatite, biofoams and biogels. Some implants can have associated bioactive eluting drugs such as implantable capsules or drug-eluting stents. Implant materials can be associated with specific tissue-type differentiated foetal cells for anti-fibrotic response.

The terms "delivery systems" mean any metallic or regularly used orthopedic, trauma, maxillo-facial natural or synthetic implant materials, hydrogels, silicones or grafts providing a means to transfer foetal cells or foetal cell products alone or in association with an implant to treat tissue or render implant.

The term "cartilage tissue" is used herein as that term is generally recognized in the art, and refers to a specialized type of dense connective tissue comprising cells embedded in an ECM (see, for example, Cormack, 1987, Ham's Histology, 9th Ed., J. B. Lippincott Co., pp. 266-272). The biochemical composition of cartilage differs according to type; however, the general composition of cartilage comprises chondrocytes surrounded by a dense ECM consisting of collagen, proteoglycans and water. Several types of cartilage are recognized in the art, including, for example, hyaline cartilage, articular cartilage, costal cartilage, fibrous cartilage, meniscal cartilage, elastic cartilage, auricular cartilage, and yellow cartilage. The production of any type of cartilage is intended to fall within the scope of the invention. According to an embodiment, the invention is directed to compositions and methods for the production of new cartilage tissue for use preferably in humans. However, the invention may also be practiced so as to produce new cartilage tissue for use in any mammal in need thereof, including horses, dogs, cats, sheep, pigs, among others. The treatment of such animals is intended to fall within the scope of the invention.

The term "tendon tissue" is used herein as that term is generally recognized in the art, and refers to a specialized type of fibrous connective tissue, comprising mainly collagen, proteoglycans and water.

The term "skin tissue" is used herein as that term is generally recognized in the art, and refers to a specialized type of fibrous tissue also comprising collagen, elasitin, and proteoglycans In one embodiment of the present invention, it is disclosed a non-enzymatic method to liberate mechanically and rapidly early adherent cell populations that define the characteristics of a parental cell bank (PCB) establishment. In some embodiments, the primary, differentiated cells come from specific cartilage tissue, from specific tendon tissue and from specific skin tissue. The development of the PCB allows consistent and stable further cell banking to be accomplished.

Thus according to an embodiment of the present invention, it is provided an in vitro non-enzymatic method for isolation, expansion and development of foetal cells selected from the group consisting of foetal epiphyseal chondrocytes, foetal Achilles tenocytes or foetal skin fibroblasts, comprising the steps of:
 a) using foetal sample selected from ulnar foetal cartilage comprising foetal epiphyseal chondrocyte; foetal Achilles tendon comprising foetal Achilles tenocytes; or foetal abdominal skin comprising foetal skin fibroblasts;
 b) micro-dissecting and dispersing said ulnar foetal cartilage, foetal Achilles tendon or foetal abdominal skin sample by mechanical attachment to scalpel scored surface;
 c) culturing said ulnar foetal cartilage, foetal Achilles tendon or foetal abdominal skin sample in vitro under conditions wherein said foetal epiphyseal chondrocytes, foetal Achilles tenocytes or foetal abdominal skin fibroblasts proliferate,
 d) selecting and isolating first adherent foetal epiphyseal chondrocyte cell populations, first adherent foetal Achilles tenocyte cell populations and first adherent foetal skin fibroblast populations therefrom.

Preferably ulnar foetal cartilage sample is a sample of foetal proximal ulnar epiphysis.

In a specific embodiment, the invention relates to a method for the isolation, expansion and development of a foetal epiphyseal chondrocyte or chondro-progenitor (FEC), foetal Achilles tendon progenitor, and foetal skin progenitor parental cell banks from a single tissue donation (only 0.2-2 cm tissue). The source of cartilage, tendon and skin is important to establish consistent cell banks Applicants have found that ulnar foetal cartilage is a superior source than from tibia, femur or rib cartilage, that foetal Achilles tendon is superior and foetal skin from abdomen is superior. Foetal cartilage, tendon and skin have remarkable abilities for repair and foetal cells exhibit immune-modulatory activity and significant wound healing capabilities. For cartilage, these aspects, in combination with their natural osteochondrogenic ability following epiphyseal ossification and the cellular characterization of FECs make this population of cells isolated in non-enzymatic method of the present invention a very interesting cellular choice for osteochondral and/or cartilage tissue repair and regeneration.

Traditional primary culture methods of digestion for liberation of the cell population of choice are not used in the method of the invention. Digestion is made generally from tissues that do not dissociate automatically (i.e. blood cellular components, some placenta tissue sections, some umbilical cord sections). Mechanical dissection of tissue combined with directed tissue/cell growth along incisions into the tissue culture plates, selects the first adherent cell population in several days of growth only and this population is very consistent and homogenous. These cell populations grow more rapidly and have different morphological and physiological profiles from other cell populations that have been digested enzymatically. Applicant has shown growth differences in 2D for foetal skin tissue which has been enzymatically digested compared to mechanical treatment with cell alignment on surface.

Importantly, if the primary cultures are developed without digestion of tissue, the foetal articular chondrocytes, foetal tendon progenitors and foetal skin progenitors cannot de-differentiate into other cell lineages easily. Chondrocytes or chondro-progenitors, tendon progenitors and skin progenitors developed without enzymatic digestion in the cell banking procedure do not differentiate into neural, adipogenic and full osteogenic cells such as mesenchymal stem cells derived from bone marrow or from foetal articular cartilage cells that have been treated enzymatically for their primary cell culture or that do not have solid tissue components to attach to plastic culture dishes. Another important aspect is that the developed cell banks from the non-enzymatic cell primary cell culture results in cells that are more stable over passages in vitro. Morphology and chromosome stability are important factors for using these banked cells for therapeutic agents in humans.

The thorough cGMP isolation using a non-enzymatic method and processing combined with the observed homogeneity and stability of this FEC population, the tendon progenitor population and the skin progenitor population in culture allows for the reliable expansion of FECs, tendon progenitors and skin progenitors for in vitro and development of extensive Master Cell Banks from the PCB population of this described method. It also makes it possible to use the same cell bank of each tissue for clinical applications of hundreds of thousands of patients, opening the door to novel osteochondral, musculoskeletal and skin regeneration therapies.

Musculoskeletal tissues, such as tendon, bone, muscle, disc and cartilage, and skin tissues when derived from fetal tissues of 10-16 weeks are ideal sources to develop parental cell banks rapidly for clinical use. The cells derived when the tissue is not enzymatically digested and when cell alignment is directed along serrated surfaces, are prepared rapidly (within 12-14 days versus several weeks to months when the tissue is subjected to enzymatic digestion), are uniform in population and maintain characteristics of specific tissue-to-cell type with associated bio-markers.

The non-enzymatic method of the present invention provides different cells than those obtained by known enzymatic methods. Thus in an embodiment, the present invention provides a foetal epiphyseal chondrocyte cell line, obtained by the non-enzymatic method of the present invention, having the designation FE002-Cart and deposited under accession number ECACC 12070303-FE002-Cart on 3 Jul. 2012. In another embodiment, the present invention provides foetal Achilles tenocyte cell line (also denoted herein as foetal Achilles tendon progenitors cell line), obtained by the non-enzymatic method of the present invention, having the designation FE002-Ten and deposited under accession number ECACC 12070302-FE002-Ten on 3 Jul. 2012. In a further embodiment, the present invention provides foetal skin fibroblast cell line (also denoted herein as foetal skin progenitors cell line), obtained by the non-enzymatic method of the present invention, having the designation FE002-SK2 and deposited under accession number ECACC 12070301-FE002-SK2 on 3 Jul. 2012.

Once established, a culture of foetal epiphyseal chondrocytes or chondro-progenitors may be used to produce chondrocytes capable of producing new cartilage cells and tissue. Differentiation of foetal epiphyseal chondrocyte to chondrocytes, followed by the production of cartilage tissue therefrom, can be triggered by the addition to the culture medium with or without the use of specific exogenous growth factors, such as, for example, BMPs such as BMP-13 or TGF-β, with or without ascorbate. The same procedures from established foetal tendon progenitors and foetal skin progenitors can be applied.

The invention further contemplates the establishment and maintenance of cultures of chondrocytes as well as mixed cultures comprising both foetal epiphyseal chondrocyte and chondrocytes. As with foetal epiphyseal chondrocyte, once a culture of chondrocytes or a mixed culture of foetal epiphyseal chondrocyte and chondrocytes is established, the population of cells is mitotically expanded in vitro by passage to fresh medium as cell density dictates, under conditions conducive to cell proliferation without cartilage formation, such as, for example, in culture medium lacking TGF-β or other growth factor. As with cultures of pre-chondrocytes, cultures of chondrocytes and mixed cultures of foetal epiphyseal chondrocyte and chondrocytes should be transferred to fresh medium when sufficient cell density is reached. Thus, formation of a monolayer of cells should be prevented or minimized, for example, by transferring a portion of the cells to a new culture vessel and into fresh medium. Such removal or transfer should be done in any culture vessel which has a cellular monolayer exceeding about 25% confluency. Alternatively, the culture system can be agitated to prevent the cells from sticking. The same method can be equally applied for foetal tendon progenitors and foetal skin progenitors.

In a further embodiment of the invention, a population of foetal epiphyseal chondrocytes or chondro-progenitors isolated from ulnar foetal cartilage is mitotically expanded and cultured in vitro to give rise to chondrocytes which can produce cartilage tissue and cells for therapeutic use. The same method can be equally applied for foetal tendon progenitors and foetal skin progenitors. Thus in an embodiment, the present invention relates to foetal epiphyseal chondrocyte (FEC), foetal Achilles tenocytes and foetal skin fibroblasts obtained by the non-enzymatic method of the invention for use as therapeutic agents.

In another embodiment of the invention, foetal epiphyseal chondrocytes or chondro-progenitors isolated from ulnar foetal cartilage, are cryopreserved and stored frozen in a "bank" from which they can be thawed and used to produce cartilage tissue and cells as needed. The foetal epiphyseal chondrocytes or chondro-progenitors, which are harvested or produced therefrom, can be stored frozen in a "bank" for a period of years. The cells may be withdrawn from the bank as needed by thawing, and the thawed cells can be used to produce new tissues and cells at any time for the repair, replacement or augmentation of cartilage, as well as other mesenchymal tissues, such as bone, tendon or ligament. The same method can be equally applied for foetal tendon progenitors and foetal skin progenitors.

As a result of the "foetal" nature of the cells isolated from ulnar foetal cartilage sample, immune rejection of the implanted foetal epiphyseal chondrocyte of the invention, or cartilage tissue produced therefrom, may be minimized. Accordingly, in another embodiment of the invention, such cells are useful as "ubiquitous donor cells" for use in any subject in need thereof. The same characteristics can be equally seen for foetal tendon progenitors and foetal skin progenitors.

In another embodiment of the invention, the foetal epiphyseal chondrocyte or chondro-progenitor cells, foetal Achilles tendon progenitors or foetal skin progenitors are suspended in a hydrogel solution where they can be either injected or implanted into a patient. Alternatively, the cells may be first seeded into the hydrogel, and then cultured prior to implantation. Preferably, the cells are cultured in the hydrogel so that they mitotically expand prior to implantation.

In yet another embodiment of the invention, new cartilage tissue and cell populations are prepared from the foetal epiphyseal chondrocyte or chondro-progenitor cells of the invention and is used to repair, replace or augment cartilage tissue in a subject using any technique of repair, replacement or augmentation known in the art or to be developed in the future. For example, the foetal epiphyseal chondrocyte or chondro-progenitors cells of the invention may be seeded onto a three-dimensional framework or scaffold composed of a biocompatible non-living material having interstitial spaces, openings or pores that can be bridged by the chondrocytes. Under appropriate in vitro culture conditions, the seeded cells substantially envelope the three-dimensional framework and secrete an extracellular matrix to form a new, living cartilage tissue which can be implanted in vivo. Alternatively, the foetal epiphyseal chondrocyte or chondro-progenitor cells of the invention are seeded onto a three-dimensional framework and immediately implanted at a site in the subject. The seeded cells proceed to form new cartilage tissue in vivo or stimulate receiver cartilage to repair and re-organize. The same method can be equally applied for foetal tendon progenitors and foetal skin progenitors in the means to form or stimulate new tendon tissue or new skin tissue of the receiver tendon or skin to repair and re-organize.

In yet another embodiment, the three-dimensional framework on which the cells of the invention are seeded further comprises, or is coated with, one or more bioactive agents or other compounds selected from the group consisting of anti-inflammatories, growth factors, immunosuppressants, etc.

In yet another embodiment of the invention, the foetal epiphyseal chondrocyte or chondro-progenitor cells of the invention are inoculated and grown on a three-dimensional framework and placed in a container that can be manipulated to allow intermittent pressure changes, or in a bioreactor system specially designed for the in vitro production of cartilage tissue constructs, which bioreactor allows for pressurization of the chamber during growth and an adequate supply of nutrients to chondrocytes by convection. The same method can be equally applied for foetal tendon progenitors and foetal skin progenitors.

Scaffold based cell therapy provides a palpable advantage in that the therapeutic tissue-generating agent delivered, in this case the cells, are easily localized and can therefore be implanted arthroscopically along with the scaffold (Iwasa et al., 2009). This bypasses the need for major invasive surgery (total joint replacement) and preserves the native tissue as best as possible, thereby significantly reducing the occurrence of inflammation, which may very well negatively affect the outcome of the therapy (van Osch et al., 2009). In order to provide a template supporting 3D tissue growth, one has to carefully tailor a scaffold's structure and composition. Synthetic materials such as polyethylene glycol (PEG), polylactic acid (PLA) and polyglycolic acid (PGA) as well as naturally derived materials such as hyaluronan, chondroitin sulfate and chitosan have been used with or without further chemical modification and side group addition in order to generate bone and cartilage (Ahmed et al., 2010; Chung et al., 2008; Khan et al., 2008).

Biomaterial scaffolds function as the extracellular matrix to provide a physical structure to protect cells and to guide tissue growth. Integration into the matrix is essential to have a three-dimensional system for delivery to the surgical site of interest. Foetal cells, unlike adult and mesenchymal cells, have been shown to penetrate throughout various biomaterials due to their inherent adhesion and migration properties. This allows for rapid seeding of the cells into the respective biomaterials and less manipulation of the implants before implantation. Different materials and fabrication methods can form biomaterial scaffolds with distinct properties which can adapt to cartilage tissue engineering. Many biodegradable biomaterials and hydrogels have been developed for other surgical purposes such as hemostatic sponges and tissue fillers (Mast et al., 1993; Patino et al. 2002; Drury and Moony, 2003). These biomaterials provide clinical-grade materials (classified as Medical Devices) to be tested for biocompatibility and to assure that there are no radical derivative products produced by the association of the biomaterial delivery system and the cellular products.

In a further embodiment, the foetal epiphyseal chondrocyte or chondro-progenitor cells of the invention are administered directly to a site in vivo, e.g., by injection and without attachment to a three-dimensional framework, to produce new cartilage tissue and cell populations at that site. The same method can be equally applied for foetal tendon progenitors and foetal skin progenitors. Thus in an embodiment, the present invention relates to use of foetal epiphyseal chondrocyte (FEC) obtained by the non-enzymatic method of the invention for the production of new cartilage tissue and/or three dimensional constructs; use of foetal Achilles tenocytes obtained by the non-enzymatic method of the invention for the production of new tendon tissue and/or three dimensional constructs and use of foetal skin fibroblasts obtained by the non-enzymatic method of the invention for the production of new skin tissue and/or three dimensional constructs.

In a further embodiment of the invention, the foetal epiphyseal chondrocyte or chondro-progenitor cells of the invention are stimulated to produce cartilage using exogenously supplied growth factors such as, for example, TGF-β or BMPs such as BMP-2, BMP-12 and BMP-13.

In yet another embodiment of the invention, the foetal epiphyseal chondrocyte or chondro-progenitor cells of the invention can be genetically engineered to produce, or to increase production of, specific types of growth factors, peptides, proteins or other molecules that serve to increase the amount of cartilage produced, or that improve the success of implantation, for example, by reducing the risk of rejection or inflammation associated with the implant. The same method can be equally applied for foetal tendon progenitors and foetal skin progenitors.

The invention also relates to the products of the foregoing methods, including but not limited to, the foetal epiphyseal chondrocyte or chondro-progenitor cells of the invention, mitotically expanded or otherwise; new cartilage tissue produced therefrom; extracellular matrix extracted therefrom; and three-dimensional cartilage/framework constructs. The invention also relates to the use of these cells, constructs and tissues in vivo to repair, replace or augment cartilage, or in vitro to form three-dimensional cartilage cultures which are useful to produce new cartilage tissue or bioactive agents, or to test the cytotoxicity of potential therapeutic agents. The same method can be equally applied for foetal tendon progenitors and foetal skin progenitors.

In an embodiment of the present invention, the foetal epiphyseal chondrocytes or chondro-progenitors isolated from ulnar foetal cartilage, as well as the chondrocytes differentiated therefrom, can be used to produce new cartilage tissue and cells to repair or replace cartilage. The same method can be equally applied for foetal tendon progenitors and foetal skin progenitors which can be used to produce new tendon or skin tissues and cells to repair or replace tendon or skin.

In a further embodiment of the present invention, the foetal epiphyseal chondrocytes or chondro-progenitors isolated from ulnar foetal cartilage according to the method of the present invention, as well as the chondrocytes differentiated therefrom, can be used as therapeutic agent. Preferably, the foetal epiphyseal chondrocyte isolated from ulnar foetal cartilage according to the method of the present invention, as well as the chondrocytes differentiated therefrom, are for use in the method for osteochondral repair (including cartilage repair and tendon repair) and regeneration, and in method for treating osteochondral diseases or defects (including osteochondral lesions, injuries, trauma, fragmentations and fractures, subchondral bone necrosis and osteochondritis) and/or arthritis. The same method can be equally applied for foetal tendon progenitors and foetal skin progenitors for specific treatments of tendon and skin.

Thus in an embodiment, the present invention relates to foetal epiphyseal chondrocyte (FEC) obtained by the non-enzymatic method of the invention for use in a method for repair and regeneration of osteochondral tissue and musculoskeletal tissue; foetal Achilles tenocytes obtained by the non-enzymatic method of the invention for use in a method for repair and regeneration of tendon tissue and musculoskeletal tissue; and foetal skin fibroblasts obtained by the non-enzymatic method of the invention for use in a method for repair and regeneration of skin tissue and for treating burns, wounds and fibrotic condition.

In a further embodiment of the present invention, is provided foetal epiphyseal chondrocyte (FEC) obtained by the non-enzymatic method of the invention for use in a method for treating osteochondral diseases or defects, arthritis and musculoskeletal diseases; foetal Achilles tenocytes obtained by the non-enzymatic method of the invention for use in a method for treating musculoskeletal diseases and tendonopathies; foetal skin fibroblasts obtained by the non-enzymatic method of the invention for use in a method for treating skin diseases.

The use of foetal epiphyseal chondrocytes (FEC) or chondro-progenitors for osteochondral tissue engineering is very promising. Indeed, throughout foetal development, the epiphysis becomes the major site for the secondary ossification centre (SOC), which transforms the FEC condensate into both an articular cartilaginous region and what becomes epiphyseal trabecular bone and marrow after vascular invasion (Blumer et al., 2008; Onyekwelu et al., 2009). It is known that foetal cartilage, such as that seen for foetal skin, has a remarkable capability for self-repair. In a foetal goat model, defects have been shown to repair with out scar or fibrous tissue formation (Namba et al., 1998).

The cells (foetal epiphyseal chondrocytes or chondro-progenitors and chondrocytes) and cartilage tissues of the invention may be used in vitro to screen a wide variety of compounds for effectiveness and cytotoxicity of pharmaceutical agents, growth/regulatory factors, anti-inflammatory agents, etc. To this end, the cells of the invention, or tissue cultures described above, are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the number of living cells in vitro, e.g., by total cell counts, and differential cell counts. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed. Thus the foetal epiphyseal chondrocytes or chondro-progenitors isolated from ulnar foetal cartilage can be also used to develop advanced therapeutic agents and/or medical device for the treatments of arthritic, osteochondral defects, cartilage repair, tendon repair. The same method can be equally applied for foetal tendon progenitors and foetal skin progenitors which can be also used to develop advanced therapeutic agents and/or medical device for the treatments of musculoskeletal tissues.

Thus in an embodiment of the present invention, it is provided a screening method for development of therapeutic agents and/or medical devices for the treatment of arthritic, osteochondral defects, cartilage repair, tendon repair, musculoskeletal tissue repair and skin repair, comprising the use of foetal epiphyseal chondrocyte (FEC), foetal Achilles tenocytes or foetal skin fibroblasts obtained by the non-enzymatic method of the invention.

The cells (foetal epiphyseal chondrocytes or chondro-progenitors and chondrocytes) and cartilage tissues of the invention may be used as model systems for the study of physiological or pathological conditions. For example, joints that are immobilized suffer relatively quickly in a number of respects. The metabolic activity of chondrocytes appears affected as loss of proteoglycans and an increase in water content are soon observed. The normal white, glistening appearance of the cartilage changes to a dull, bluish color, and the cartilage thickness is reduced. However, the amount of this change that is due to nutritional deficiency versus the amount due to upset in the stress-dependent metabolic homeostasis is not yet clear. The cells and cartilage tissues of the invention may be used to determine the nutritional requirements of cartilage under different physical conditions, e.g., intermittent pressurization, and by pumping action of nutrient medium into and out of the cartilage construct. This may be especially useful in studying underlying causes for age-related or injury-related decrease in tensile strength of articular cartilage, e.g., in the knee, that predispose the weakened cartilage to traumatic damage. The same method can be equally applied for foetal tendon progenitors and foetal skin progenitors useful in studying underlying causes for age-related or injury-related decrease in tensile strength of tendon and skin to traumatic or age-related damage.

The cells (foetal epiphyseal chondrocytes or chondro-progenitors and chondrocytes) and cartilage tissues of the invention may also be used to study the mechanism of action of cytokines and other pro-inflammatory mediators, e.g., IL-1, TNF and prostaglandins, that are released into the synovial fluid as a result of rheumatic disease. Thus, the patient's own joint fluid could be tested in vitro to study the effects of these compounds on growth of the cells of the invention. In addition, cytotoxic and/or pharmaceutical agents can be screened for those that are most efficacious for a particular patient, such as those that reduce or prevent resorption of cartilage or otherwise enhance the balanced growth of articular cartilage. Agents which prove to be efficacious in vitro could then be used to treat the patient therapeutically. The same method can be equally applied for foetal tendon progenitors and foetal skin progenitors useful in studying mechanism of action of growth factors, cytokines and other pro-inflammatory mediators which cause an imbalance in tissue repair.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

The foregoing description will be more fully understood with reference to the following Examples. Such Examples are, however, exemplary of methods of practicing the present invention and are not intended to limit the scope of the invention.

Examples

The proximal ulnar epiphysis, the Achilles tendon and abdominal skin were processed following strict transplantation laws and by-laws and guidelines for organ donation and screening to create FEC, tendon and skin parental cell banks for tissue engineering applications (CHUV Ethics Committee protocol #62/07). The tissue biopsies (cartilage, ~2 mm$^3$, tendon, ~0.2 mm$^3$, skin, ~2 cm$^2$) were micro-dissected and dispersed by mechanical attachment to scalpel scored surfaces. (No enzymatic treatments were used to assure only adherent cartilage, tendon or skin outgrowth and consistency of cell population: necessary criteria for clinical usage). FEC, tendon and skin outgrowth was observed at 1-2 days to one week and expansion was accomplished at one and at two weeks. The parental cell bank was established with 50-200 vials of $5$-$10 \times 10^6$ cells and stored in the vapour-phase of liquid nitrogen. In vitro characterization of isolated cells exhibit a remarkable homogeneity in mono-layer culture as well as a notable proliferative potential with a propensity for overlapping (3D culture). FECs, tendon progenitors and skin progenitors do not seem to exhibit notable phenotypic variations within the first six passages. FEC and tendon progenitors are able to spontaneously coalesce when placed in pellet culture form, deposit matrix and express fundamental chondrogenic or tenocyte markers. Flow cytometric analyses revealed unimodal distributions indicative of a homogenous population. A comparison with adult bone marrow derived MSCs yielded FEC or tendon surface marker profiles consistent with a chondrogenic or tenocyte rather than an undifferentiated progenitor phenotype.

Foetal Chondrocyte, Tendon Progenitor and Skin Progenitor Cell Banking, Characterization in Relation to Therapeutic Agent Preparation.

Cell Banking

Cell banks have been established in the University Hospital of Lausanne from foetal biopsies between 12-14 weeks of gestation obtained after pregnancy termination with informed and written consent and approval from the local Medical School Ethics Committee since 1993 and more particularly for clinical cell banks since 2007. Pre-clinical articular cartilage cell banks have been successfully developed from 2 independent donors to date. Using one of these (FE002-Cart p.0, FE-002-Ten p.0, FE-002-SK2, p.0), it will be possible to establish all of the cells necessary for pre-clinical and clinical trials at low passages (MCB at p.3 and WCB at p.5).

Figure 7:
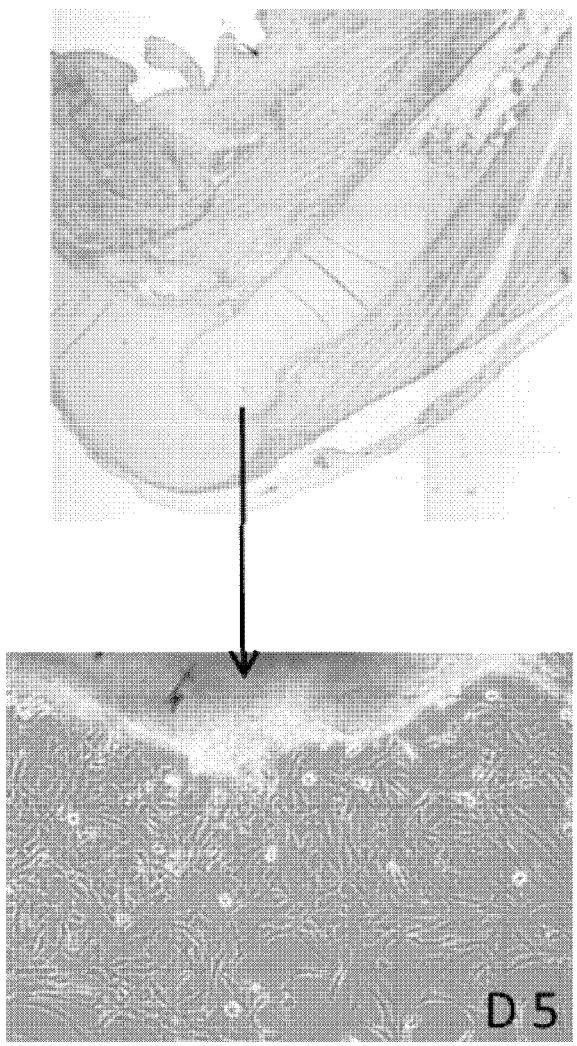
FIG. 7 shows processing of proximal ulnar epiphysis tissue to begin Parental Cell Bank production for foetal chondro-progenitors (foetal epiphyseal chondrocytes) and cell selection at Day 6 showing consistency.

From ~0.3 $cm^3$ articular cartilage (radius) (see FIG. 7), from ~0.2 $mm^3$ Achilles tendon and from ~1 $cm^2$ abdominal skin, pre-clinical cell banks were prepared at passages 0 and 1. Tissue was dissected into <0.5 $mm^3$ fragments, where possible, and grown in DMEM supplemented with 10% FCS and glutamine and the cells were used for characterization and experimentation at passage 3 and 6 or 1 and 9. They were grown to confluence before splitting and rinsed twice with PBS and counted.

Detailed Procedure without Enzymatic Processing:

The tissue was divided into two, 10 cm plates with whole tissue fragments ~5 per plate (<0.5 $mm^3$), where possible. Tissue culture dishes were previously scored deeply with a sterile scalpel in a check-board pattern under the laminar flow hood. Tissue fragments were placed into the scored plastic regions mincing gently and attaching the fragments within the plastic indentions. A small quantity of nutrient media was placed around each fragment to avoid floating of tissues for the first 24 hours. Following the first 24 hours, 8 ml of culture media was added onto each 10 cm plate and this was changed two times per week before passage. These fragments were grown in DMEM supplemented with only 10% foetal bovine serum (Hyclone) to help insure a consistent cell culture. Cell cultures were grown at 37° C. in a humidified atmosphere of 95% air/10% $CO_2$. It is important to mention that any nutrient component necessary for cell culture for clinical trials should have thorough safety requirements and tracing. All animal derived products, such as for foetal bovine serum and trypsin, specific clinical lots of trypsin and gamma irradiated serum that have been tested for adventitious agents should be employed. Cell growth was first seen even following one day but after cell growth advanced during 5-7 days, dishes of tissue and cells were removed from plates either by trypsinizing (0.25% trypsin-0.1% ethylene diaminetetraacetic acid [EDTA]) or with EDTA alone to passage to multiple tissue culture flasks or frozen for cell banking. At this point, some foetal cartilage, foetal tendon or foetal skin cells were frozen into individual units in liquid nitrogen and others were passaged at 1,000-2,000 cells/$cm^2$ or 10,000-50,000 cells/$cm^2$ for producing the PCB. Cells were centrifuged at 2000 g for 15 min and resuspended in a freezing solution of DMEM (5 ml)+FCS (4 ml)+DMSO (1 ml, Fluka) and frozen in 1 ml aliquots (~5-10 million cells) at −80° C. in Nalgene Cryo 1° C. Freezing Container's (Nalgene) to achieve a −1° C./min rate of cooling and freezing curve. After 24 hr, cells were transferred to liquid nitrogen for longer storage.

1-2 vials of pre-clinical foetal articular cartilage, foetal tendon or fetal skin are used to prepare a consistent Working Cell Bank (WCB) for characterization. Procedure design is the same as that used in cGMP manufacturing. In short, cells are initiated at 1,500 cells/$cm^2$, or from 1,000-100,000 cells/$cm^2$ into 100 cell culture flasks (T75, Nunc) with 15 ml of nutrient media (DMEM+10% clinical grade serum, foetal bovine, Invitrogen). Cells have the media changed every 2 days and the production/expansion of cells is done for 10-14 days at 37° C., 10% humidity or for 3-6 days at higher density seedings. At day 12-14, batches of 10 T75 flasks are subjected to TrypLE to separate the cells from the flasks and placed into centrifuge tubes. An equal volume of nutrient media is added to each tube before centrifugation to buffer TrypLE effects. The cell pellet obtained from all of the flasks are resuspended into 200 ml freezing media solution (DMEM, Serum, DMSO, 5:4:1 ratio) and aliquoted into 100 Nunc freezing viles (1.5 ml) at a dilution of $10\times10^6$ cells/ml.

Cells are frozen at −80° C. in Nalgene Cryo 1° C. Freezing Container's (Nalgene) to achieve a −1° C./min rate of cooling and freezing curve. After 24 hr, cells are transferred to liquid nitrogen in the gas phase. This WCB is at passage 2 and used for cell characterization and cells are used at various passages but mainly between 2-8.

Foetal Chondrocyte Characterization: Identity, Stability, Consistency, Genetic Stability Banked foetal chondrocytes have been compared throughout Applicants' study to BM-MSC cells that have been banked under the same technical conditions in their lab. MSC's are allogenic cells and one of the main other cell type that have been proposed and used in pre-clinical and clinical experimentation for cartilage regeneration among other tissues (however, mesenchymal cells are not tissue specific and have to be programmed to make other tissue types). Moreover, MSC's are more instable and have to be used under passage 4. The same method can be equally applied for foetal tendon progenitors and foetal skin progenitors Foetal Cartilage Characterization Compared to BM-MSC Foetal articular cartilage cell banks have been characterized by surface markers accomplished with FACS analysis, functional assays for matrix deposition compared to BM-MSC cells. Foetal cartilage cells derived from articular epiphyseal tissue have been isolated and parental cell banks have been frozen.

Some markers that have been compared in preliminary experiments include:

CD105: Endoglin. Part of TGFBeta receptor complex. Main criterion for MSC positive selection.

CD90: Thy-1. Main criterion for MSC positive selection.

CD44: PTPRC. Leukocyte marker. Criterion for negative selection of bmMSCs.

CD73: NT5E. Main criterion for MSC positive selection.

CD166: ALCAM.

Figure 8:
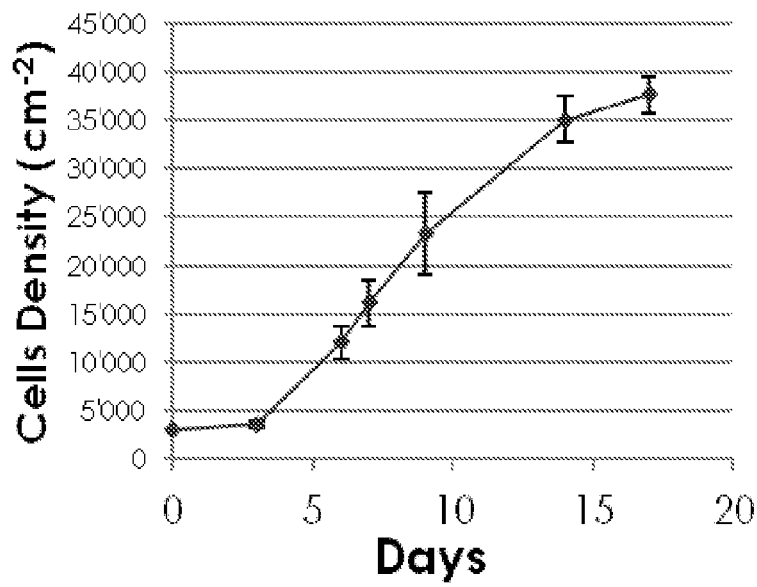
FIG. 8 shows cell growth of foetal chondro-progenitors (foetal epiphyseal chondrocytes) following low density seeding (~2000 cells/cm$^2$) and recovery of frozen cell stocks at Day 6 and 12 showing high stability, consistency and maintained function.
Figure 8:
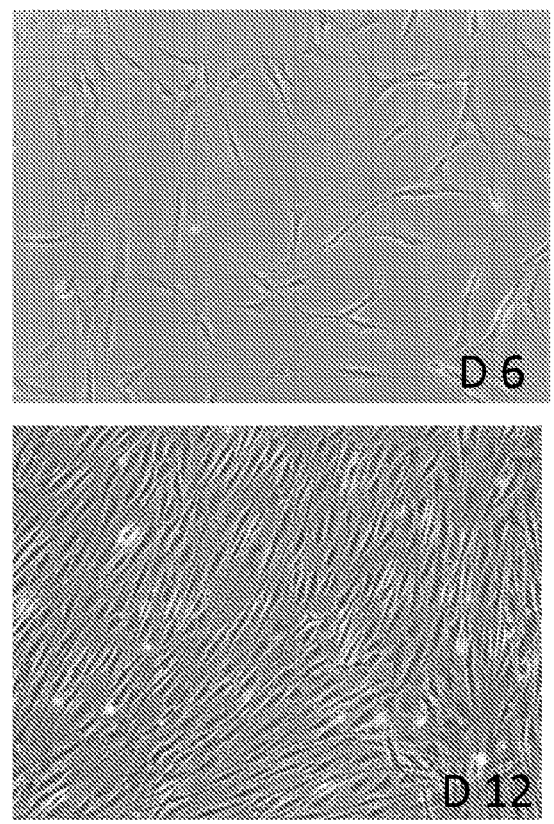
Figure 9:
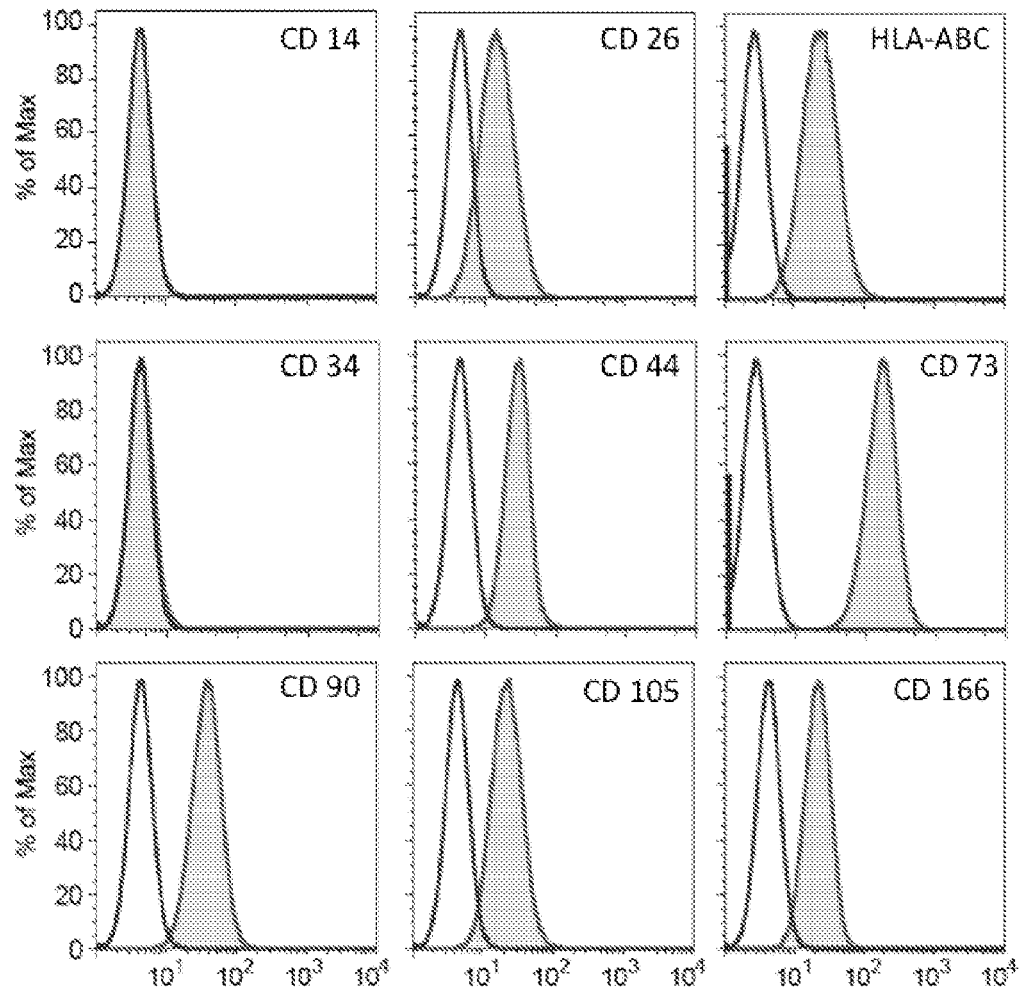
FIG. 9 shows FACS analysis and 3D matrix deposition characteristics for foetal chondro-progenitors (foetal epiphyseal chondrocytes).
Figure 9:
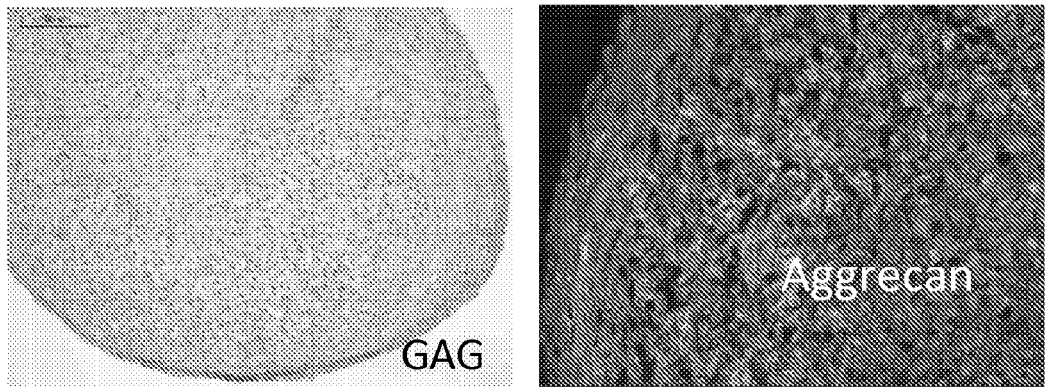
Figure 10:
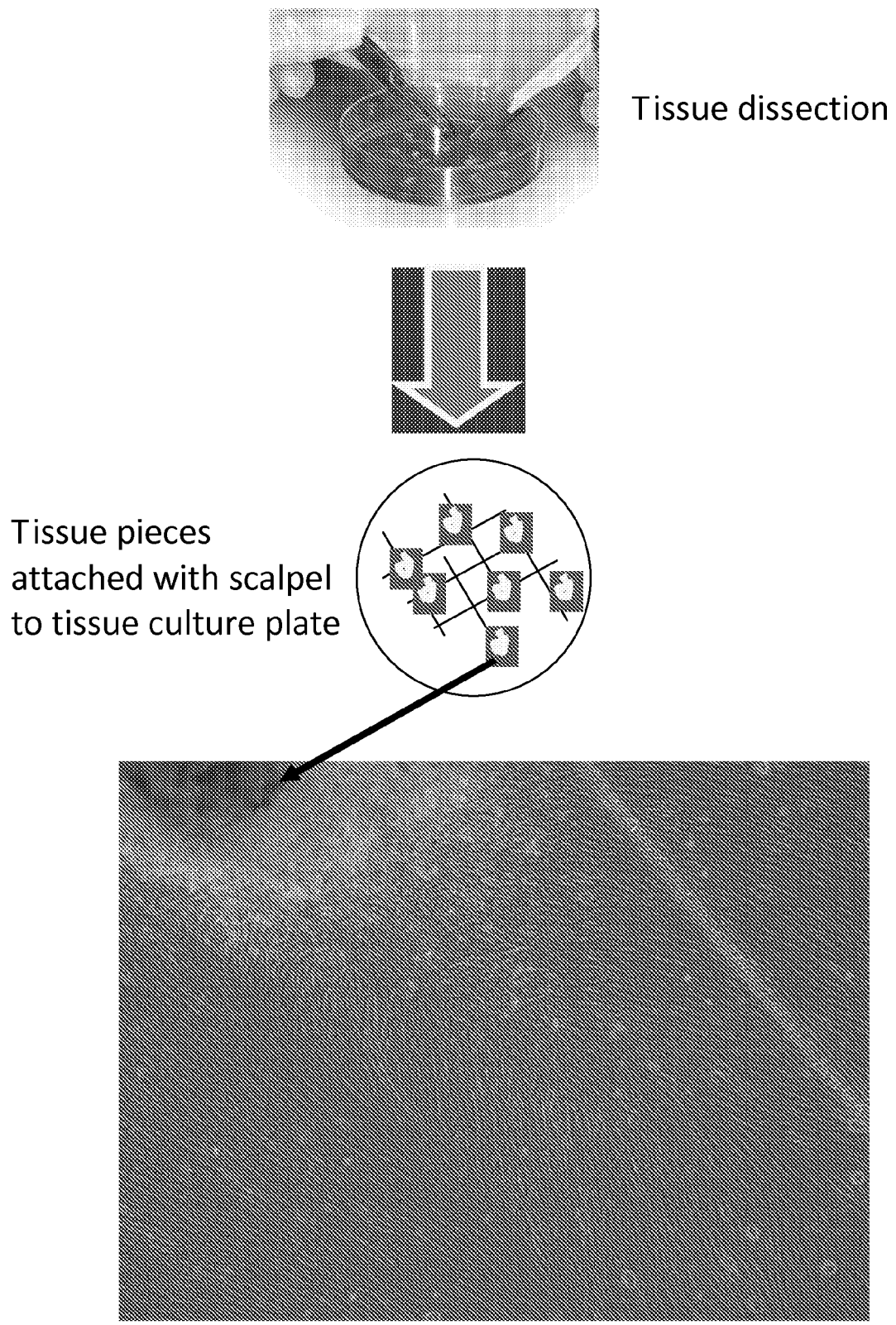
FIG. 10 shows foetal cell progenitor cell expansion on tissue culture plastic directed along mechanical scored-plated.
Figure 11:
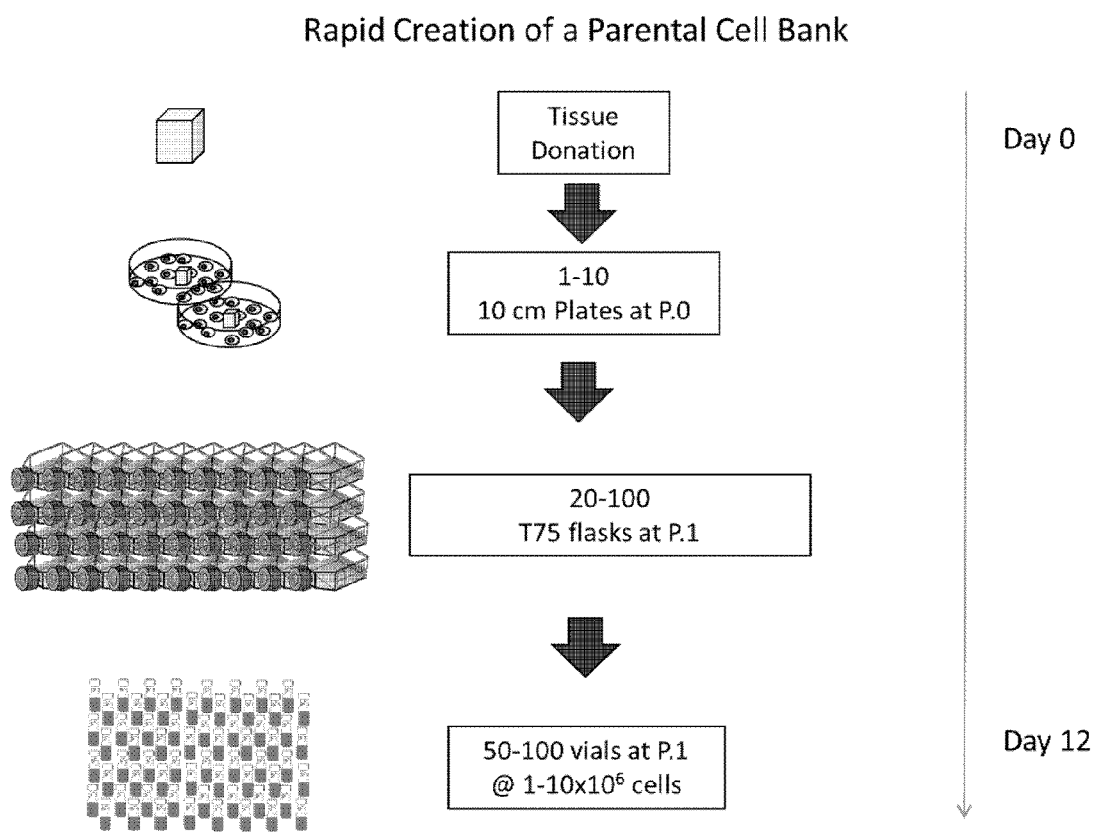
FIG. 11 shows rapid development of clinical parental cell banks using non-enzymatic preparation of tissue.

(See FIGS. 8 and 9)

The same method can be equally applied for foetal tendon progenitors and foetal skin progenitors Biocompatibility: Foetal Cartilage Biocompatibility with Hydrogels and Matrix Different matrixes that are available for medical use are initially tested for biocompatibility. Hydrogels of various compositions, collagens and some biodegradable polymers are used in the first experiments. For hydrogels, cells are cultivated within the gel that is inserted into a pre-prepared agar mold. This is necessary to avoid cellular attachment to the tube and to allow three dimensional growth. The mold is prepared by pipetting 1 ml of melted agarose (20% agar, low-melting agar) inside a 1.5 ml sterile conical eppendorf centrifuge tube for which a 0.5 ml sterile conical eppendorf centrifuge tube is inserted into the liquid agar and allow to solidify before extracting the 0.5 ml tube leaving a conical inset. Following gel and cell addition, 100 µl media is pipetted onto the surface of each tube and media changed two times weekly. Cells are grown for one, two and four weeks in a 37° C. incubator at 95% relative humidity and 10% $CO_2$.

For matrix preparations, preliminary experiments investigating cell seeding density (from $10^3$ to $10^4$ cells $cm^2$) and growth periods (from 1 to 28 days) are performed in order to determine optimal conditions for foetal cell delivery. Foetal cells and BM-MSC's at passages 3 or 4 (maximum 4 for MSC due to instability thereafter) are placed in 10 ml media (DMEM containing 10% FBS) and seeded on matrix. The matrix containing the cells is placed into a 37° C. incubator at 95% relative humidity and 10% $CO_2$. An additional 30 ml media is then added one hour later. Matrix is changed twice weekly with nutrient media. Biocompatibility is also measured by a contact assay where cells are cultured within a tissue culture plate where hydrogel or matrix were initially seeded. Cell growth and migration are analysed visually with respect to hydrogel and matrix interface. Following one, two and four weeks, samples are stained with giemsa and photographed (Sony CyberShot DSC-570, Zeiss macro lens, Zoom 6×, 3.3 megapixels).

The invention claimed is:

1. A scaffold comprising of a biocompatible, non-living material having an interstitial space inoculated with a foetal epiphyseal chondrocyte (FEC) cell belonging to a cell line having the designation FE002-Cart and deposited under accession number ECACC 12070303-FE002-Cart.

2. A scaffold comprising of a biocompatible, non-living material having an interstitial space inoculated with a foetal Achilles tenocyte cell belonging to a cell line having the designation FE002-Ten and deposited under accession number ECACC 12070302-FE002-Ten.

3. A scaffold comprising of a biocompatible, non-living material having an interstitial space inoculated with a foetal skin fibroblast cell belonging to a cell line having the designation FE002-SK2 and deposited under accession number ECACC 12070301-SK2.

4. A method of producing new cartilage tissue and/or three dimensional constructs, the method comprising culturing the FEC cell in the scaffold of claim 1.

5. A method of producing new tendon tissue and/or three dimensional constructs, the method comprising culturing the foetal Achilles tenocyte cell in the scaffold of claim 2.

6. A method of producing new skin tissue and/or three dimensional constructs, the method comprising culturing the foetal skin fibroblast cell in the scaffold of claim 3.

7. A method for repair and regeneration of osteochondral tissue and musculoskeletal tissue, the method comprising administering the scaffold of claim 1 to a subject in need thereof.

8. A method for repair and regeneration of tendon tissue and musculoskeletal tissue, the method comprising administering the scaffold of claim 2 to a subject in need thereof.

9. A method for repair and regeneration of skin tissue and for treating burns, wounds and fibrotic conditions, the method comprising administering the scaffold of claim 3 to a subject in need thereof.

10. A method for treating osteochondral diseases or defects, arthritis and musculoskeletal diseases, the method comprising administering the scaffold of claim 1 to a subject in need thereof.

11. A method for treating musculoskeletal diseases and tendonopathies, the method comprising administering the scaffold of claim 2 to a subject in need thereof.

12. A method for treating skin diseases, the method comprising administering the scaffold of claim 3 to a subject in need thereof.

13. A screening method for development of a therapeutic agent for the treatment of arthritic, osteochondral detects or musculoskeletal tissue injury, the method comprising exposing the scaffold of claim 1 to the therapeutic agent.

14. A screening method for development of a therapeutic agent for the treatment of cartilage, tendon, or musculoskeletal tissue injury, the method comprising exposing the scaffold of claim 2 to the therapeutic agent.

15. A screening method for development of a therapeutic agent for the treatment of skin injury, the method comprising exposing the scaffold of claim 3 to the therapeutic agent.

16. The scaffold of claim 1, wherein the scaffold is:
(a) a three dimensional matrix composed of one or materials selected from the group consisting of collagen, polylactic acid, polyglycolic acid, polyethylene glycol, chitosan, and elastin; or
(b) a hydrogel composed of one or more materials selected from the group consisting of hyaluronic acid, silicone, and chitosan.

17. The scaffold of claim 2, wherein the scaffold is:
(a) a three dimensional matrix composed of one or materials selected from the group consisting of collagen, polylactic acid, polyglycolic acid, polyethylene glycol, chitosan, and elastin; or
(b) a hydrogel composed of one or more materials selected from the group consisting of hyaluronic acid, silicone, and chitosan.

18. The scaffold of claim 3, wherein the scaffold is:
(a) a three dimensional matrix composed of one or materials selected from the group consisting of collagen, polylactic acid, polyglycolic acid, polyethylene glycol, chitosan, and elastin; or
(b) a hydrogel composed of one or more materials selected from the group consisting of hyaluronic acid, silicone, and chitosan.

* * * * *